(12) United States Patent
Leahy

(10) Patent No.: US 9,381,009 B2
(45) Date of Patent: Jul. 5, 2016

(54) SURGICAL DEVICE

(76) Inventor: Patrick Leahy, Dublin (IE)

( * ) Notice: Subject to any disclaimer, the term of this patent is extended or adjusted under 35 U.S.C. 154(b) by 200 days.

(21) Appl. No.: 11/587,676

(22) PCT Filed: Apr. 25, 2005

(86) PCT No.: PCT/EP2005/004502
§ 371 (c)(1),
(2), (4) Date: Aug. 7, 2007

(87) PCT Pub. No.: WO2005/102185
PCT Pub. Date: Nov. 3, 2005

(65) Prior Publication Data
US 2008/0051817 A1    Feb. 28, 2008

(30) Foreign Application Priority Data

Apr. 26, 2004   (IE) .................................. S2004/0291

(51) Int. Cl.
*A61M 29/00* (2006.01)
*A61B 17/02* (2006.01)
*A61B 17/34* (2006.01)
*A61B 19/00* (2006.01)
*A61B 17/00* (2006.01)

(52) U.S. Cl.
CPC .......... *A61B 17/0218* (2013.01); *A61B 17/3423* (2013.01); *A61B 19/38* (2013.01); *A61B 2017/00265* (2013.01); *A61B 2017/00283* (2013.01); *A61B 2017/00557* (2013.01); *A61B 2019/5206* (2013.01)

(58) Field of Classification Search
CPC ........... A61B 17/0218; A61B 17/3423; A61B 19/38; A61B 2017/00265; A61B 2017/00283; A61B 2017/00557; A61B 2019/5206
USPC .................................. 606/191, 192; 600/207
See application file for complete search history.

(56) References Cited

U.S. PATENT DOCUMENTS

| 3,782,370 | A  | * | 1/1974  | McDonald ..................... 600/207 |
| 4,984,564 | A  | * | 1/1991  | Yuen ............................. 600/207 |
| 5,480,410 | A  |   | 1/1996  | Cuschieri et al. |
| 5,640,977 | A  |   | 6/1997  | Leahy et al. |
| 5,741,298 | A  | * | 4/1998  | MacLeod ....................... 606/213 |
| 5,823,945 | A  |   | 10/1998 | Moll et al. |
| 6,402,724 | B1 | * | 6/2002  | Smith et al. ................... 604/289 |
| 7,195,590 | B2 | * | 3/2007  | Butler et al. .................. 600/207 |
| 7,766,823 | B2 | * | 8/2010  | Moll et al. ..................... 600/192 |
| 2003/0181939 | A1 |   | 9/2003 | Bonutti |
| 2007/0255256 | A1 | * | 11/2007 | Fischer et al. ............... 604/528 |
| 2008/0132908 | A1 | * | 6/2008 | Nguyen ........................ 606/122 |
| 2009/0082633 | A1 | * | 3/2009 | Kathrani et al. .............. 600/207 |

OTHER PUBLICATIONS

International Search Report dated Aug. 2, 2005 including PCT/ISA/237 (Written Opinion of the International Searching Authority), 4 pages.

* cited by examiner

*Primary Examiner* — Julie A Szpira
(74) *Attorney, Agent, or Firm* — Sullivan & Worcester LLP

(57) ABSTRACT

The present invention provides a device and method for use in laparoscopic surgery, in particular hand assisted laparoscopic surgery, the device comprising a flexible body having a sidewall of double wall construction which defines an inflatable cavity enabling the body to be inflated from a collapsed state into an expanded state, in order to distend a surgical cavity to provide an enclosure within which a surgical procedure may be performed, the body having an opened to allow communication between the enclosure defined by the body when in the expanded state and tissue/organs surrounding the body, in particular directly adjacent, in use, the open end of body.

4 Claims, 2 Drawing Sheets

SURGICAL DEVICE

Figure 1:
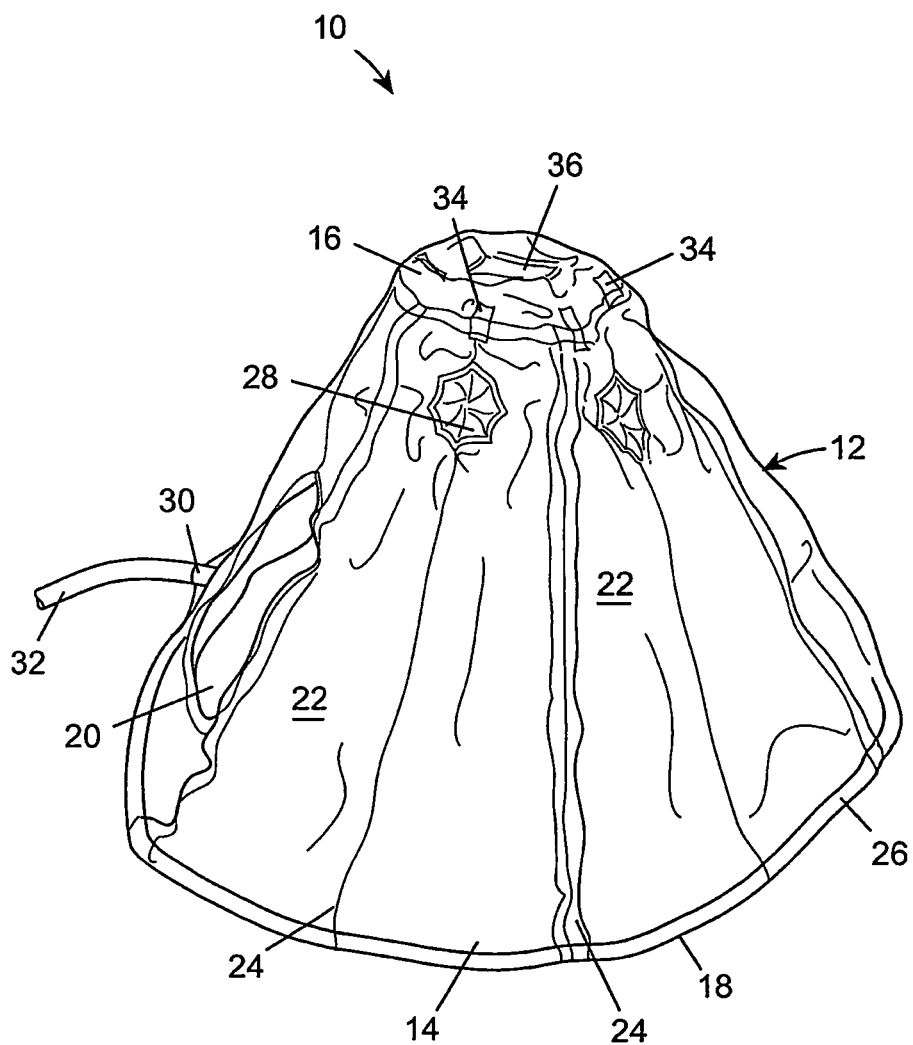

The present invention relates to a surgical device, and in particular a surgical device which may be employed during laparoscopic or hand assisted laparoscopic surgery in order to simplify same.

Although open surgery is still the most commonly performed type of surgery, it is gradually being replaced, where possible, by laparoscopic or hand assisted laparoscopic surgery, otherwise known as "keyhole" surgery. Laparoscopic, or "keyhole" surgery, involves the creation of a relatively small incision, for example in the abdomen or the like, through which incision a surgeons hand and/or surgical instruments or fibre optic cameras may be inserted, in order to operate within the body. This type of surgery is far less traumatic than open surgery, usually requires less recovery time, and also leaves significantly less scarring. Open surgery requires the creation of a large incision or a plurality of incisions to gain access to surgical cavities such as the abdominal or thoracic cavities, the skin and tissue surrounding the incisions then being drawn back to expose the tissues/organs beneath. This type of open surgery therefore enables the surgeon to gain access, using both hands, to the site to be operated on, thereby facilitating a relatively straightforward surgical procedure.

However, the benefits of open surgery are somewhat negated by the drawbacks associated with same. Primarily, the very nature of open surgery, requiring enlarged incisions and the displacement of significant amounts of tissue/organs in order to access the site in question, and perform the necessary surgery, results in significant post-operative trauma for the patient, and will also require an extended time for the incision(s) to heal. In addition, open surgery will also generally leave significant scarring, as a result of the enlarged incisions necessary.

As a result, laparascopic surgery is greatly preferred, but is not without its own complications. For example, laparoscopic surgery employs very different techniques to conventional surgery, and is generally considered to be more awkward than conventional open surgery, due to a lack of direct "hands on" contact by the surgeon. For this reason alone, many surgeons are unwilling or unable to perform this type of surgery, despite the benefits which may be achieved The most fundamental problem with laparoscopic surgery is the restrictive space within which to operate, as the site to be operated on is not exposed or openly accessible. Several solutions to this problem are currently employed, the most common solution being the use of an insufflation gas, such as carbon dioxide, which is constantly pumped into the cavity within which surgery is being performed. However this procedure adds to both the cost and complexity of the operation, and adverse reactions to the gas being used have been know to occur.

Another solution employed is the use of an inflatable bladder or balloon which, while deflated, is passed through the incision into the surgical cavity, and is then inflated in order to enlarge the cavity. However, these balloons often serve as an impediment or obstacle during surgery, and may need to be continually repositioned in order to allow suitable access to the site being operated on.

As mentioned above, the main problem associated with laparoscopic surgery is the lack of hands on contact by the surgeon, all of the surgical techniques, such as cutting, suturing, etc. being carried out remotely by means of laparoscopic surgical instruments and with the aid of fibre optic imaging systems. This problem can be significantly reduced by the use of hand assisted laparoscopic surgery, in which an incision is made, for example in the abdomen, which incision is dimensioned to permit a surgeon's hand access through the incision to the site on which surgery is to be performed, thereby allowing palpation and bio-physical feedback, thus greatly simplifying the laparoscopic surgical procedure.

However, this type of hand assisted laparoscopic surgery is not without its complications. As set out above, during conventional laparoscopic surgery, the surgical cavity is distended by means of an insufflation gas, for example carbon dioxide, generally by means of a trocar and cannula arrangement. However, with hand assisted laparoscopic surgery, the access incision for the surgeon's hand provides a ready outlet for the insufflation gases, thereby preventing the necessary build-up of pressure within the gas in order to distend the surgical cavity.

One solution to this problem is set out in U.S. Pat. No. 5,640,977. This patent sets out a method and apparatus for hand assisted laparoscopic surgery, using a sleeve which must be sealed within the access wound, and which sleeve is provided with an inflatable cuff at the end of the sleeve distal the access wound, which cuff may be inflated such as to create a seal around the surgeon's forearm when located within the sleeve. In this way, the surgical cavity can be inflated, and although gas will initially leak through the access wound into the sleeve, the sleeve, being sealed against the surgeon's arm, will soon pressurise, thereby allowing the surgical cavity to be pressurised and therefore become distended.

However, the apparatus employed is complex and time consuming to use, and still requires the pumping of an insufflation gas such as carbon dioxide directly into the surgical cavity, which has been known to have adverse effects on the patient.

The present invention therefore seeks to overcome the problems associated with the above-mentioned known solutions.

The present invention therefore provides, according to a first aspect, a laparoscopic surgical device comprising a flexible body movable between a collapsed state and an expanded state, in which expanded state the body defines an enclosure having at least one opening; and an aperture in a sidewall of the body, the aperture being shaped and dimensioned to enable the passage of a hand through the aperture.

Preferably, the body is distensible into the expanded state.
Preferably, the body is inflatable into the expanded state.
Preferably, the body is substantially transparent.
Preferably, the body is formed from a flexible polymer.
Preferably, the body comprises a reinforcing member about the at least one opening.
Preferably, the reinforcing member is flexible.
Preferably, the at least one opening is defined by an open end of the body.
Preferably, the body, when in the expanded state, is substantially hemispherical in shape.
Preferably, the body comprises at least one port which is shaped and dimensioned to allow the passage of a medical instruments therethrough.
Preferably, the body is segmented into a plurality of panels.
Preferably, the plurality of panels are individually, sequentially or simultaneously movable between a collapsed state and an expanded state.
Preferably, adjacent panels are separated by a reinforcing seam.
Preferably, the sidewall is of double wall construction defining an inflatable cavity.
Preferably, the device is adapted to receive and retain at least one biosign sensor.

Preferably, the device is adapted to receive and retain at least one light source in a position such that, when the body is in the expanded state, the light source will direct light towards the at least one opening.

Preferably, the device comprises an elongate tube extending from the body and connectable to a remote supply of a fluid, in order to effect inflation of the body.

According to a second aspect of the present invention there is provided a method of performing hand assisted laparoscopic surgery within a surgical cavity, the method comprising the steps of;

providing a surgical device according to the first aspect of the invention;

passing the device, in a collapsed state, into the surgical cavity;

moving the body into an expanded state; and passing a hand through the aperture in the sidewall of the body to gain access to the surgical cavity.

Preferably, the method comprises, in the step of moving the body into the expanded state, inflating the body to effect the expansion.

Preferably, the method comprises the further step of passing a medical instrument at least partially through the port in the sidewall into the surgical cavity.

Preferably, the method comprises the further step of illuminating the surgical cavity.

As used herein, the term "enclosure" is intended to mean an area bounded by a sidewall or the like, which enclosure has however at least one open end or side which allows communication between the interior of the enclosure and the surrounding area, in particular the area directly adjacent the open end or side. Such an enclosure could take the form of an open ended dome, an open ended box or cylinder, or any other three dimensional space.

As used herein, the term "hand" is intended to mean a human hand, as well as, a robotic or mechanical hand.

As used herein, the term "distensible" is intended to mean the ability to distend or expand/deform/displace outwardly in order to be capable of enlarging a visceral space within a surgical cavity, in particular for the purposes of aiding laparoscopic surgical procedures, and may be achieved by inflation, mechanical displacement, or by any other suitable means.

As used herein, the term "inflation" is intended to mean the act of inflating an object with a fluid, whether with a gas or a liquid.

As used herein, the term "port" is intended to mean an aperture or opening through which a medical instrument may pass, in particular a medical instrument such as laparoscopic medical instrument, a fibre optic camera, etc.

As used herein, the term "biosign" is intended to mean any signal relating to or resulting from a biological or physiological process, such as blood pressure, heart rate, electrical activity, a bioacoustic signal, or the like.

Figure 2:
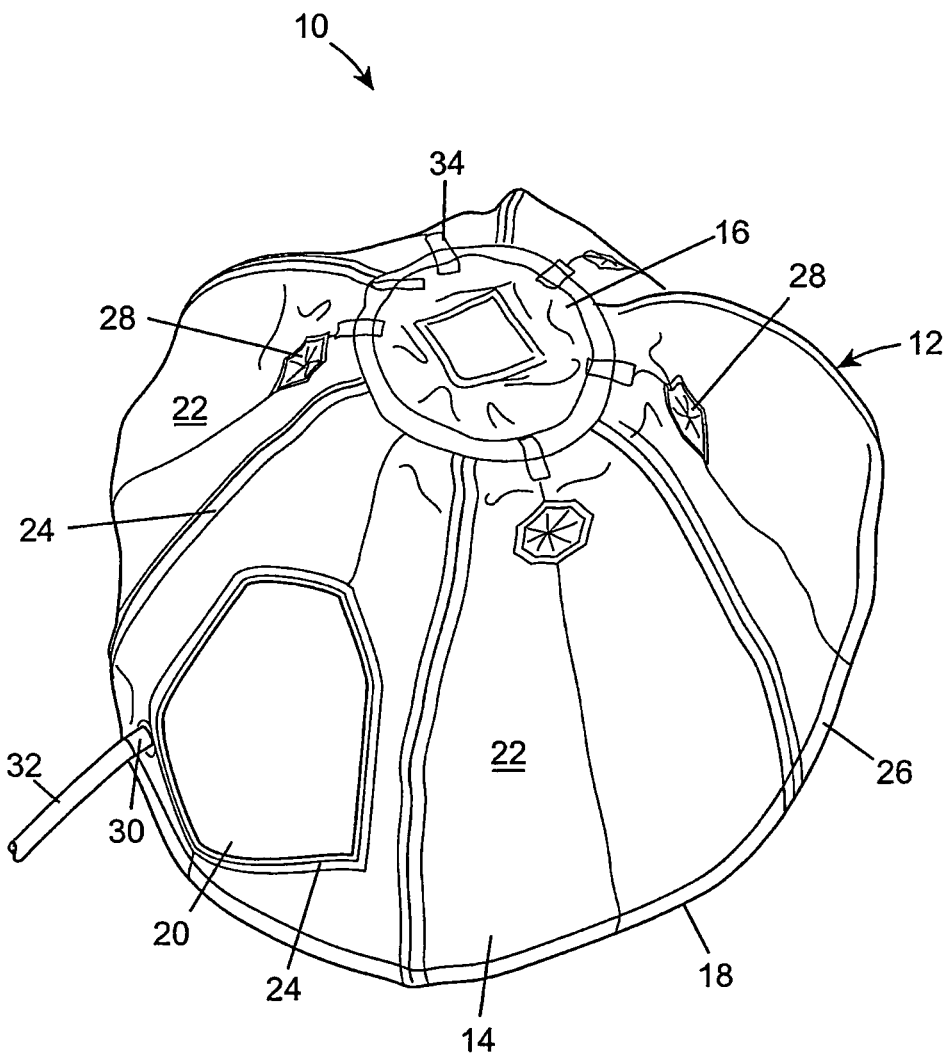

The present invention will now be described with reference to the accompanying drawings, in which;

FIG. 1 illustrates a perspective view of the surgical device of the present invention, in a collapsed state; and FIG. 2 illustrates a perspective view of the surgical device of FIG. 1, in an expanded or inflated state.

Referring now to the accompanying drawings, there is illustrated a surgical device, generally indicated as 10, for use as a surgical aid when performing minimally invasive surgery such as hand assisted laparoscopic surgery, or any other form of surgery which involves the location of a surgical instrument or a surgeon's hand (not shown) within a restricted surgical cavity in order to perform a surgical procedure, in particular hand assisted laparoscopic surgery within the abdominal cavity. The device 10 comprises a flexible body 12 which may be displaced, in particular inflated, from a collapsed state as shown in FIG. 1, to an expanded state as shown in FIG. 2, in order to create or define an enclosure bounded by the body 12. Thus the device 10 may be used to effect distension of the abdominal cavity, or any other surgical cavity, from the interior thereof, in order to create a space or enclosure within which a surgeon can perform the necessary surgical procedure(s). The device 10 therefore facilitates the distension of a surgical cavity, for example the abdominal cavity, while avoiding the need to introduce an insufflation gas directly and continually into such a cavity, thereby greatly simplifying, and reducing the cost of, any operation previously requiring such direct insufflation.

The device 10 is preferably inserted through a conventional keyhole incision (not shown), for example in the abdomen, in the collapsed state, and once in the correct position, may be inflated in order to distend the abdomen. In this regard, it should be noted that, for the purposes of clarity, the device 10 as illustrated in FIG. 1 is shown deflated, but not fully collapsed or compressed, as would be the case immediately prior to insertion into the abdominal cavity or the like. The flexible nature of the body 12 allows same to be rolled or folded up into a very small volume, in order to facilitate the insertion of the device 10 through the small "keyhole" incisions employed in laparoscopic surgery, or indeed by any other suitable access opening (not shown). To this end it may be preferably to actively evacuate the body 12, for example using a vacuum pump (not shown) or the like, in order to allow the device 10 to be collapsed or compressed into the smallest possible volume. It may also be desirable to then provide a retaining sleeve or sheath (not shown) or the like around the collapsed device 10, in order to maintain the device 10 in the fully collapsed state. Such a retaining sleeve could then be removed once the device 10 is correctly positioned within the surgical cavity. Alternatively, the retaining sleeve (not shown) could be formed from a cellulose material or the like, which simply splits or ruptures on inflation of the body 12, for example as manufactured by Inamed Corporation, Santa Barbara, Calif., the United States.

The body 12 comprises a sidewall 14 joined to a top 16, each being of double wall configuration, defining a fluid tight cavity therebetween, similar to a double glazing window panel, which cavity may be filled with a pressurised fluid, in particular a gas such as air, in order to inflate the device 10. The body 12, in the preferred embodiment illustrated, is essentially hemispherical or domed shaped, thus defining an opening in the form of an open end 18 which, when the device 10 is inflated, allows the internal organs to be contacted from within the enclosure defined by the device 10. It will of course be understood that the body 12 could be of any other suitable shape which retains the functionality thereof, namely defining an enclosure from which access may be gained to the internal organs and/or tissue to be operated on.

The sidewall 14 is therefore provided with at least one aperture 20 therein, which is shaped and dimensioned to permit the passage of a hand therethrough, preferably a human hand. Thus when the device 10 is in place within the abdominal cavity, and inflated, the device 10 is preferably positioned such that the aperture 20 is adjacent the surgical incision in the abdomen through which the device 10 was inserted. A surgeon may therefore pass his hand through the surgical incision, and into the interior of the body 12 via the aperture 20. The device 10 will therefore act as a shield or support, retaining the surrounding tissue/organs out of contact with the area to be operated on, namely the area in communication with the open end 18 of the body 12.

It is possible to vary the degree of inflation of the body 12, thereby varying the volume of the cavity created therein. Therefore, should a surgeon be of the opinion that fully inflating the body 12, and therefore substantially distending the abdominal cavity, may result in damage to the surrounding tissue for one reason or another, the surgeon can elect to only partially inflate the body 12. Conversely, if the surrounding tissue/organs in contact with the sidewall 14 and top 16 are exerting significant pressure thereon, the body 12 can be fully inflated, and the pressure within same increased in order to maintain the structural rigidity of the body 12 in the inflated state.

To further increase the structural rigidity of the body 12, the sidewall 14 is preferably formed from a number of panels 22, adjacent panels 22 being separated by a respective seam 24. The seams 24 may be formed by radio frequency welding, or by any other suitable means, for example by the use of an adhesive or the like. This segmented construction, along with the seams 24, adds significant strength and rigidity to the body 12, helping the body 12 to maintain its intended shape during use. In this regard, it will be appreciated that the body 12 could be of any suitable shape, other than the preferred hemispherical shape shown. However, the hemispherical shape provides no sharp corners or edges, and thus facilitates a gradual stretching of the abdominal cavity, with no corners or edges protruding into the surrounding delicate tissue.

To further increase the strength and rigidity of the body 12 when inflated, the open end 18 is preferably provided with a reinforcing member in the form of a flexible ring 26 secured thereto. The ring 26 helps to maintain the circular footprint of the device 10 when inflated, but the flexibility of the ring 26 enables the device 10 to be folded up when in the collapsed or uninflated state.

The body 12 is also preferably provided with at least one, and preferably a plurality of ports 28, which in the embodiment illustrated are located at an upper portion of each panel 22, adjacent the top 16. The outer edge of each of the ports 28 is sealed in order to prevent gas from leaking from the body 12, again preferably using radio frequency welding. The ports 28 are designed to enable surgical instruments (not shown), or a fibre optic camera (not shown) or the like, to be passed through the body 12 into the interior thereof, in order to assist in the surgical procedure(s) being performed. The ports 28 can be shaped, dimensioned, and positioned as required, in order to suit the intended function of same. In use, in addition to the incision made to allow the insertion of the device 10, and the subsequent insertion of a surgeon's hand, one or more additional incisions (not shown) may be required in the patient's abdomen in order to facilitate the insertion of the above mentioned medical instruments (not shown) through one or more of the ports 28. However, as these incisions need only be dimensioned to allow the passage of relatively small surgical instruments (not shown), as opposed to a surgeon's hand, said incisions will quickly heal following completion of the surgical procedure, and will generate little if any trauma at the surgical site, and will should not therefore retard the patients recovery.

In order to effect inflation of the body 12, a nozzle 30 projects from the sidewall 14, to which nozzle 30 is connected a tube 32, which in use passes back through the surgical incision in the abdomen, and is connected to a remote gas supply, such as a simple pump. A one way valve (not shown) is preferably provided, either in the nozzle 30 or in the tube 32, in order to prevent the body 12 from deflating during use. Alternatively, the fluid supply to the body 12 could be maintained at pressure during use of the device 10, in order to prevent deflation of the body 12. If a one way valve is provided, means must be provided to enable deflation of the body 12 subsequent to use of the device 10. It will also be apparent that some form of pump (not shown), such as a hand operated bladder or the like, could be provided on the device 10, in fluid communication with the body 12, in order to render the device 10 independent of external pumps or gas supplies. Alternatively, it would be possible to provide a small reservoir or canister (not shown) of pressurised air or the like on the device 10 and in fluid communication with the body 12, which could be remotely actuated in order to inflate the body 12.

In the embodiment illustrated, the seams 24 seal adjacent panels 22 from one another, and thus during inflation of the body 12, the gas pumped through the tube 32 will first enter the panel 22 containing the aperture 20. The gas will then flow into the top 16, from which extends a channel 34 into each panel 22. Thus the gas can pass from the top 16 through the respective channel 34, into each panel 22, thereby inflating the entire body 12. It will of course be appreciated that the seams 24 could be omitted, or be intermittent in form, in order to allow the panels 22 to be in fluid communication with one another. It will also be appreciated that the top 16 could be omitted, and the entire body 12 formed as a single surface or panel. In addition, it is envisaged that the plurality of panels 22 could be individually, sequentially or simultaneously inflated by suitable means, for example by provided a plurality of inflating tubes (not shown), one for each panel 22. In this way the expanded or inflated shape of the body 12 could be slightly altered by deflating or partially deflating one or more of the panels 22, in order to give a desired shaped, or to lessen the pressure exerted by one or more of the panels 22 on a sensitive area of tissue/organ or the like.

The device 10 is also preferably provided with at least one pocket 36, which although located in the top 16 in the preferred embodiment illustrated, may be located at any suitable position on the body 12. The pocket 36 is designed to receive and retain a biosign sensor (not shown) adapted to read various biosigns of the patient, for example from the peritonial fluid and the cellular elements within the abdomen.

The body 12 is preferably manufactured from a flexible, transparent polymer such as medical grade urethane. The use of a flexible material for the body 12 will prevent or at least minimise the possibility of damage/injury to a patient (not shown) while the device 10 is initially being inserted into a surgical cavity, and again when being withdrawn therefrom. It will be appreciated that there are a large number of materials or combinations thereof, which would be suitable for use in manufacturing the body 12. For example, the body 12 could conceivably be formed from a fabric, but is preferably formed from a polymer, for example a medical grade polyurethane, as manufactured by Dow Corning, of Michigan, the United States, such polyurethane preferably being of a thickness of between 50 μm and 150 μm.

As fibre optic cameras are typically employed during laparoscopic surgical procedures, and as mentioned above, the body 12 is preferably transparent, in order to allow the full illumination of a surgical cavity created by distension of the body 12, in addition to permitting the visualisation of tissue/organs through the sidewall 14. In addition, the sidewall 14 is preferably formed from a non-absorbent or a liquid impermeable material, as otherwise the device 10 would be significantly more difficult to clean/sterilise following each operation. However, the device 10 could be manufactured as a disposable item, to be discarded after a single use.

It will be appreciated that the use of a transparent material for the body 12, allowing the visualisation of surrounding tissue/organs, would allow the device 10 to be used solely for diagnostic purposes. When used in this capacity, it would be possible to use a smaller "keyhole" incision than would be required when access for a surgeon's hand is necessary, as the incision need only be sized to allow the passage of the device 10 therethrough, when in the fully collapsed state. Once the device 10 is positioned and inflated in the desired location, a fibre optic camera (not shown) may then be used to scan the surrounding tissue/organs for signs of damage/disease or the like. As the device 10 need only accommodate a fibre optic camera when used for diagnostic purposes, the device 10 may be downsized and thus dimensioned to be accommodated in otherwise inaccessible areas of the body. Due to the smaller incision required for this diagnostic application, and the lack of any surgery actually being performed, such a diagnostic procedure would be relatively minor and would require little if any recovery time, and would leave essentially no scarring.

As mentioned above, it is conventional practice, and typically essential, to use a fibre optic camera (not shown) or the like, during laparoscopic surgical procedures. The device 10 is therefore preferably provided with means (not shown) for guiding a fibre optic camera and/or a light source (not shown), preferably a fibre optic based light source, into a position on the body 12 which will enable the illumination and visualisation, in use, of the tissue/organs located adjacent the open end 18, thereby allowing the clear visualisation of said tissue/organs and the surgeon's hand and/or medical instrument(s) during any surgical procedure. The guiding means (not shown) could for example take the form of a simple tube (not shown) running along the inwardly facing surface of the sidewall 14, the tube (not shown) being dimensioned to receive a fibre optic camera or the like. It is also envisaged that the device 10 could be provided with a stand alone light source and/or camera (not shown) which may be remotely operated, although such components would require a dedicated power source such as a battery or the like to be provided on the device 10, which would add to the complexity and cost of the device 10.

The surgical device 10 of the present invention thus provides a means by which insufflation gases are contained within a reservoir, in particular the body 12 of the device 10. Thus the cost and complexity associated with a continual leakage of gas from a surgical cavity are avoided. Furthermore, adverse reactions and complications associated with introducing $CO_2$ or the like directly into the abdominal cavity or other surgical cavity can be avoided. The device 10 may also be used for diagnostic purposes, allowing the visualisation of tissue/organs with a view to determining the condition thereof.

The invention claimed is:

1. A method of performing hand assisted laparoscopic surgery within a surgical cavity, the method comprising the steps of:
   providing a surgical device comprising a flexible body movable between a collapsed state, in which collapsed state the body is fully insertable, through a surgical incision, into a surgical cavity, and an expanded state, in which expanded state the body is substantially hemispherical in shape and defines an enclosure having at least one opening defined by an open end of the hemispherical body; and an aperture in a sidewall of the body, the sidewall being of double wall construction defining an inflatable cavity therebetween, said sidewall being sufficiently distensible to distend the cavity an amount which will allow hand assisted surgery to be performed within the cavity without the use of insufflation gas in the surgical cavity, and the aperture being shaped and dimensioned, and positioned relative to the opening, to enable the passage of a hand through the aperture to access a surgical site via the opening;
   passing the device, in a collapsed state, through a surgical incision into the surgical cavity;
   moving the body into an expanded state by inflating the cavity defined by the double wall sidewall such as to distend the cavity an amount which will allow hand assisted surgery to be performed within the cavity without the use of insufflation gas in the surgical cavity; and
   passing a hand through the aperture in the sidewall of the body to gain access to the surgical cavity via the opening.

2. A method according to claim 1 comprising, in the step of moving the body into the expanded state, inflating the body to effect the expansion.

3. A method according to claim 1 comprising the further step of passing a medical instrument at least partially through a port in the sidewall into the surgical cavity.

4. A method according to claim 1 comprising the further step of illuminating the surgical cavity.

* * * * *